(12) United States Patent
Cannell et al.

(10) Patent No.: US 6,221,389 B1
(45) Date of Patent: *Apr. 24, 2001

(54) AQUEOUS CARRIER SYSTEMS FOR WATER-INSOLUBLE MATERIALS

(75) Inventors: David W. Cannell, New York, NY (US); Hiten Mathur, Woodbridge, NJ (US); Nghi Nguyen, Edison, NJ (US); Cynthia Espino, Princeton, NJ (US); Mick Swanborough, Avenel, NJ (US); Mohamed Kanji, Edison, NJ (US); Carl Orr, Scotch Plains, NJ (US); Lila Patel, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/445,343

(22) PCT Filed: Jun. 9, 1998

(86) PCT No.: PCT/US98/10617

§ 371 Date: Jan. 11, 2000

§ 102(e) Date: Jan. 11, 2000

(87) PCT Pub. No.: WO98/56333

PCT Pub. Date: Dec. 17, 1998

Related U.S. Application Data

(63) Continuation-in-part of application No. 08/871,524, filed on Jun. 9, 1997, now Pat. No. 6,015,574.

(51) Int. Cl.[7] .................................................. A61R 9/10
(52) U.S. Cl. ............................ 424/450; 516/145; 514/54
(58) Field of Search ........................... 424/450; 510/145; 514/54

(56) References Cited

U.S. PATENT DOCUMENTS

| | | |
|---|---|---|
| 3,996,146 | 12/1976 | Tarasov et al. . |
| 4,174,296 | 11/1979 | Kass . |
| 4,874,553 | 10/1989 | Hager et al. . |
| 5,002,761 | 3/1991 | Mueller et al. . |
| 5,160,739 | 11/1992 | Kanga . |
| 5,173,303 | 12/1992 | Lau et al. . |
| 5,783,554 | 7/1998 | Li et al. . |
| 5,804,203 | 9/1998 | Hahn et al. . |
| 6,013,269 | * 1/2000 | El-Nokaly et al. ................... 424/401 |
| 6,022,547 | * 2/2000 | Herb et al. ........................... 424/401 |
| 6,033,680 | * 3/2000 | Dixon et al. ......................... 424/401 |
| 6,051,250 | * 4/2000 | Ribier et al. ......................... 424/450 |

FOREIGN PATENT DOCUMENTS

| | | |
|---|---|---|
| 895 719 A1 | 7/1983 | (BE) . |
| 0 123 071 A2 | 10/1984 | (EP) . |
| 0 340 592 A2 | 11/1989 | (EP) . |
| 0 521 799 A1 | 1/1993 | (EP) . |
| 0 605 951 A1 | 7/1994 | (EP) . |
| 0 868 898 A1 | 10/1998 | (EP) . |

OTHER PUBLICATIONS

Ribosa et al., "Physico–chemical Modifications of Liposomes Structures Through Interaction With Surfactants," *International Journal of Cosmetic Science*, pp. 131–149 (1992).

* cited by examiner

*Primary Examiner*—James H Reamer
(74) *Attorney, Agent, or Firm*—Finnegan, Henderson, Farabow, Garrett & Dunner, L.L.P.

(57) ABSTRACT

A composition containing at least one organic phospholipid capable of forming bilayers in aqueous solution; at least one amphoteric surfactant; and at least one nonionic surfactant present in an amount by weight equal to or greater than the amount of the phospholipid. The invention also relates to a delivery system for water-insoluble ingredients containing the above components, at least one water-insoluble ingredient, and an aqueous phase, wherein the organic phospholipid, amphoteric surfactant, and nonionic surfactant are present in a combined amount sufficient to allow the water-insoluble ingredient to be incorporated into the system. A method of treating keratinous susbstances is also disclosed.

60 Claims, 5 Drawing Sheets

AQUEOUS CARRIER SYSTEMS FOR WATER-INSOLUBLE MATERIALS

STATEMENT OF RELATED APPLICATIONS

Figure 1:
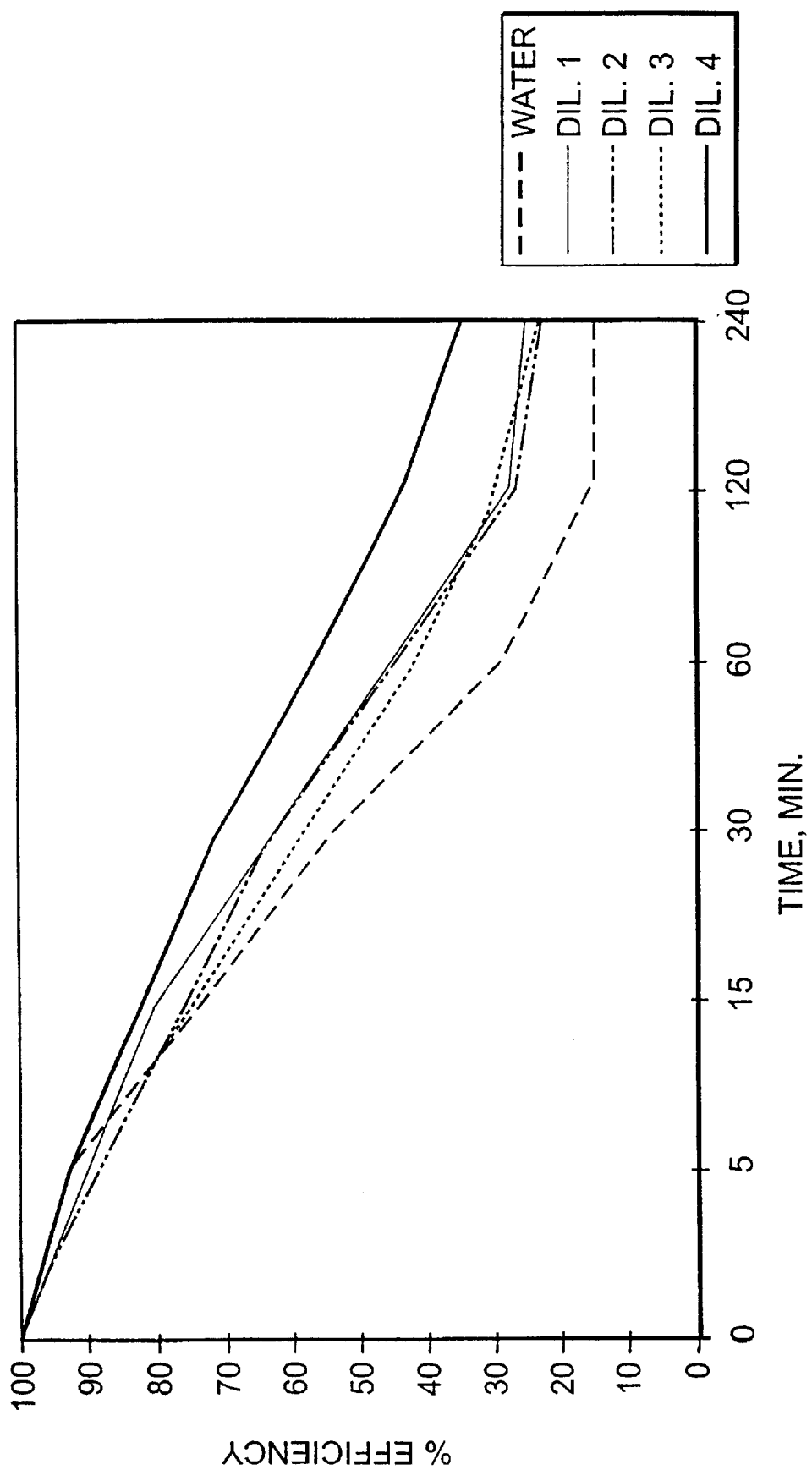

This application is a continuation-in-part of U.S. application Ser. No. 08/871,524, filed Jun. 9, 1997, now U.S. Pat. No. 6,015,574, which is hereby incorporated by reference in its entirety.

TECHNICAL FIELD

The present invention relates to novel carrier systems based on organic phospholipids capable of forming bilayers in aqueous solution, nonionic surfactants, and amphoteric surfactants, wherein these carrier systems allow water-insoluble materials such as lipophilic materials and water-insoluble polymers, resins, or latexes to be incorporated into aqueous solutions.

BACKGROUND ART

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphipathic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods utilize alcohol for cosolubilization. Alcohol solutions can have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. Ribosa et al., in "Physico-chemical modifications of liposome structures through interaction with surfactants," Int'l Journal of Cosmetic Science 14:131–149 (1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, these phospholipids are toxicologically safe. It would thus be desirable for cosmetic and pharmaceutical applications to provide delivery systems that include such organic phospholipids as a carrier for other lipophilic ingredients, without the need for alcohols and other similar solvents.

In addition to solubilizing lipophilic ingredients such as oils, vitamins, and ceramides in aqueous systems, it would be desirable to solubilize other water-insoluble ingredients, specifically unneutralized or partially neutralized polymers, resins, or latexes, in aqueous delivery systems. U.S. Pat. No. 5,391,368 to Gerstein teaches solubilization of a hair-styling polymer in a composition comprising an anionic surfactant and an amphoteric surfactant. According to Gerstein, it is the amphoteric surfactant which dissolves the water-insoluble styling polymer because the polymer is not soluble in the anionic surfactant alone.

Gerstein presents some problems, however. Many hair care and hair setting products are formulated at acidic pH because of a desire for such products to be compatible with the pH of the scalp and hair surface. Gerstein does not disclose a pH at which its system is formulated, but if the Gerstein system is acidified, the polymer will precipitate out of solution. In addition, the Gerstein system does not carry and there is no suggestion that it could carry any additional lipophilic ingredients in its mixture of anionic surfactant, amphoteric surfactant, and styling polymer. Further, Gerstein does not describe the incorporation of its styling polymer into any products other than the disclosed styling shampoo, nor does Gerstein suggest that such incorporation would be possible.

Thus, there remains a need for an aqueous delivery system that can solubilize water-insoluble materials, in particular, lipophilic materials, unneutralized or partially neutralized polymers, resins, or latexes, where these water-insoluble materials will not precipitate out of solution upon acidification, where the amount of deposition of water-insoluble material can be controlled, and where the system could carry other ingredients in addition to the water-insoluble ingredient. For example, it would be beneficial to have a system which incorporates water-insoluble materials into compositions containing other ingredients, such as dyeing and permanent wave compositions. The present invention provides such a delivery system.

DISCLOSURE OF THE INVENTION

In order to achieve these and other advantages, the present invention is drawn to a composition made up of at least one organic phospholipid capable of forming bilayers in aqueous solution, at least one amphoteric surfactant, and at least one nonionic surfactant. The nonionic surfactant is present in an amount equal to or greater than the amount of the organic phospholipid.

In another embodiment, the present invention relates to an aqueous delivery system for water-insoluble materials. The delivery system (or "carrier") includes the above-described composition in addition to at least one water-insoluble ingredient, and an aqueous phase. The nonionic surfactant is present in an amount equal to or greater than the amount of the organic phospholipid. The organic phospholipid, the amphoteric surfactant, and the nonionic surfactant are present in a combined amount sufficient to allow the water-insoluble ingredient to be incorporated into or solubilized by the delivery system. The present invention is also drawn to a process for the preparation of an aqueous system comprising: (a) combining at least one organic phospholipid capable of forming bilayers in aqueous solution, at least one nonionic surfactant, and at least one amphoteric surfactant to form a mixture, (b) heating the mixture obtained in step (a), (c) adding an aqueous solution to form a diluted mixture, and (d) cooling the diluted mixture. Water-insoluble ingredients can be incorporated in step (a).

Finally, in yet another embodiment, the present invention is drawn to a method for treating keratinous substances. First an aqueous solution is prepared containing at least one organic phospholipid capable of forming bilayers in aqueous solution; at least one amphoteric surfactant; at least one nonionic surfactant present in an amount by weight equal to or greater than the amount of the phospholipid; and at least one water-insoluble ingredient. The phospholipid, amphoteric surfactant, and nonionic surfactant are present in a combined amount sufficient to allow the water-insoluble ingredient to be incorporated into the aqueous solution. The aqueous solution is then applied to the keratinous substances.

Reference will now be made in detail to the present preferred embodiment(s) of the invention.

BEST MODE FOR CARING OUT THE INVENTION

Advantageously, the present invention allows water-insoluble materials or ingredients to be solubilized in an aqueous solution. No alcohol is required for cosolubilization, and there is no need for liposome preparation. Further, when the water evaporates, the residue left behind includes the water-insoluble material and/or the phospholipid.

The composition of the invention is also easy to formulate and is gentle on the hair, skin, or eyelashes because the surfactants used are generally mild. Unlike the attempted solubilization of phospholipids in the prior art, the present invention requires the presence of at least one nonionic surfactant and at least one amphoteric surfactant in the concentrated solutions of phospholipid.

The compositions and delivery systems of the present invention readily deposit the organic phospholipid/water-insoluble substances on the hair, skin, and eyelashes, and, because of their inherent insolubility, resist being washed off with water. Accordingly, these compositions and delivery systems can be used in hair shampoos, conditioners, hair dyeing compositions, including oxidative dyes and bleaches, permanent waving compositions, curl relaxing compositions, hair setting compositions, bath and body products, sunscreens, or cosmetics such as mascaras and foundations.

These systems can also be used to deliver active water-insoluble pharmaceutical ingredients, particularly in topical applications. Such systems could further help protect against oxidation and rancidity by protecting sensitive ingredients in pharmaceuticals or foods.

Additionally, the "load" carried by these systems can be quite high, a benefit that inures both to the user and to the manufacturer in an economic sense. Load is defined as the weight of added hydrophobe (water-insoluble material) divided by the weight of the phospholipid expressed as a percentage. Thus, 1 g of hydrophobe in a composition with 5 g phospholipid is a ⅕ or 20% load. In the art, 50% is considered a high load and can be achieved with certain hydrophobes and surfactant combinations.

Without being bound to a particular theory, the inventors believe that in the composition of the present invention, an organized structure, likely a laminar gel, is formed between the organic phospholipid and the nonionic surfactant and is solubilized by the amphoteric surfactant. The organized structure can incorporate other water-insoluble materials or hydrophobes. In aqueous systems, the structure remains organized, as evidenced by the clarity of the solution, exhibiting a slight Tyndall light scattering effect, and, when concentrated, showing lamellar anisotropic structures under polarized light.

In one embodiment, therefore, the invention is drawn to a composition comprising at least one organic phospholipid capable of forming bilayers in aqueous solution, at least one amphoteric surfactant, and at least one nonionic surfactant, where the nonionic surfactant is present in an amount by weight equal to or greater than the amount of the phospholipid. Neither the amphoteric nor the nonionic surfactant alone will give a satisfactory solution with the organic phospholipids. When dissolved in either an amphoteric or a nonionic surfactant, solubility for the phospholipid was poor compared to solubility in the mixture of surfactants of the present invention.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

In the present invention, lecithin is preferably used in an amount greater than 0 to about 5% by weight of the composition as a whole. Since lecithin itself is not a pure raw material and may have free glycerides, glycerin, fatty acids, and soaps, adjustments in this ratio may need to be made, i.e., one source of lecithin may require different ratios of nonionic and amphoteric surfactants than another to achieve maximum clarity of solution. Preferably, the composition of the invention forms a clear solution, though the purpose of the invention is achieved just as effectively with a slightly cloudy solution.

Other than lecithins, another group of phospholipids which may be useful in the present invention are multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Amphoteric surfactants are typically available for commercial sale in solution form with the active surfactant accounting for approximately 40% of the total solution weight. Cocoamphodipropionate is particularly preferred, for example, MIRANOL C2M-SF Conc. (disodium cocoamphodipropionate), in its salt-free form, available from Rhône-Poulenc. MIRANOL is sold in solution form with amphoteric surfactants composing approximately 40% of the total solution weight; for example, 10 g of MIRANOL contain about 4 g of amphoteric surfactant. Also preferred is CROSULTAINE C-50 (cocamidopropyl hydroxysultaine), available from Croda. CROSULTAINE is also sold in solution form with the amphoteric surfactant composing approximately 50% of the total solution weight. The amphoteric surfactants are preferably present in the composition in an amount ranging from about 2 to 25% by weight of the composition as a whole when 5% of the organic phospholipid, preferably lecithin, is used. When the phospholipid/amphoteric/nonionic system is employed as a carrier for a water-insoluble polymer or resin, the amphoteric surfactants are preferably present in the composition in an amount ranging from about 6 to 25% by weight. When the phospholipid/amphoteric/nonionic system is employed as a carrier for a lipophilic material, the the amphoteric surfactants are preferably present in the composition in an amount ranging from about 4 to 20% by weight. Other amphoteric surfactants useful in the present invention include disodium wheatgermimido PEG-2 sulfosuccinate, available under the trade name MACKANATE WGD from McIntyre Group Ltd., which is a solution with amphoteric surfactants composing approximately 39% of the total solution weight, and disodium soyamphodiacetate, available under the trade name MACKAM 2S from McIntyre Group Ltd., which is a solution with amphoteric surfactants composing approximately 34.5% of the total solution weight.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

Nonionic surfactants may be selected from, but are not limited to, the following:

| # of Cs | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | Arlasolve 200, available from ICI Surfactants |
| C-18 | Steareth-10 | Volpo S-10, available from Croda Chemicals Ltd. |
| C-18 | Steareth-16 | Solulan-16, available from Amerchol Corp. |
| C-18 | Steareth-20 | BRIJ 78, available from ICI Surfactants |

-continued

| # of Cs | Name | Trade Name |
|---|---|---|
| C-18 | Steareth-25 | Solulan-25, available from Amerchol Corp. |
| C-18= | Oleth-10 | BRIJ 97, available from ICI Surfactants |
| C-18= | Oleth-20 | Volpo-20, available from Croda Chemicals Ltd. |

Alkyl polyglucose surfactants sold under the name PLANTAREN, available from Henkel, may also be used. The nonionic surfactant is preferably present in an amount of about 5 to 20% by weight relative to the weight of the whole composition when 5% lecithin is used. More preferably, the nonionic surfactant is present in an amount of about 10 to 20% by weight.

In one preferred embodiment of the composition of the present invention, the organic phospholipid capable of forming bilayers in aqueous solution, the amphoteric surfactant, and the nonionic surfactant are present in the composition such that the nonionic surfactant and the amphoteric surfactant are each present in an amount by weight greater than the amount of phospholipid. In a more preferred embodiment, the amount of phospholipid in the composition is kept fixed while the amounts of the amphoteric and nonionic surfactants are increased. In a still more preferred embodiment, calculating the phospholipid as present at a value of 1, the phospholipid, amphoteric surfactant and nonionic surfactant are preferably present in the composition in a ratio ranging from about 1:0.8:2 and above by weight relative to the whole composition, i.e., where the amounts of the surfactants can be increased independently of each other but the amount of phospholipid stays fixed. The ratio is considered to be "above" 1:0.8:2 when the amount of either of the surfactants increases. When the phospholipid/amphoteric/nonionic system is employed as a carrier for a lipophilic material, the ratio preferably ranges from about 1:1.2:2 and above. When the phospholipid/amphoteric/nonionic system is employed as a carrier for a water-insoluble polymer or resin, the ratio is preferably about 1:1.2:3 and above, and more preferably above about 1:1.2:4. The loading capability for hydrophobes carried by the delivery system of the present invention is maximized if the ratio of nonionic surfactant to phospholipid is minimized, with the bilayers still being solubilized, because an excess of nonionic surfactant may disrupt the organized structure.

In one preferred embodiment, the composition of the present invention comprises ALCOLEC S (soy lecithin), MIRANOL C2M-SF Conc. (disodium cocoamphodipropionate, an amphoteric surfactant), ARLASOLVE 200 (IsoCeteth-20, a nonionic surfactant) in a ratio of 5:15:10 (which is a LAN ratio of 1:1.2:2) when a lipophilic water-insoluble ingredient is employed, and 5:15:20 (which is a LAN ratio of 1:1.2:4) when a water-insoluble polymer, resin, or latex is employed, wherein the ratios are calculated by weight relative to the whole composition. In general, the preferred compositions of the invention are known as the "LAN" because they contain a lecithin (L), an amphoteric surfactant (A), and a nonionic surfactant (N). Although lecithin is particularly preferred, the amphoteric and nonionic surfactants may vary.

When used as an ingredient in further formulations, the LAN is compatible and generally gives clear solutions with anionic surfactants such as alkyl sulfates and ethoxylated alkyl sulfates. Other anionic surfactants such as sulfosuccinates may also be used. Typically, LAN compositions can resist storage at 45° C. for three months or more, which would predict that they have a shelf life at room temperature of at least three years.

In another aspect, the present invention relates to an aqueous delivery or carrier system comprising: at least one organic phospholipid capable of forming bilayers in aqueous solution, at least one nonionic surfactant preferably present in an amount greater than or equal to the amount of the phospholipid, at least one amphoteric surfactant, at least one water-insoluble ingredient, and an aqueous phase. The lecithin, nonionic surfactant, and amphoteric surfactant are present in a combined amount sufficient to allow the at least one water-insoluble ingredient to be incorporated into or solubilized by the aqueous system. The amount sufficient for solubilization may vary depending on the type of composition; for example, shampoo and mascara formulations require a lower concentration of LAN than do conditioner, deep treatment, bleach, permanent wave, dye, and relaxant compositions.

Water-insoluble materials or ingredients include, but are not limited to the following:

(1) Lipophilic "ingredients" or "materials" such as silicones, oil-soluble vitamins such as Vitamin E and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, and laurylmethicone copolyol. The lipophilic ingredients will, for example, moisturize or condition the skin, hair, and/or eyelashes and leave behind no oily feel.

(2) Water-insoluble polymers, resins, and latexes which are unneutralized or partially neutralized, wherein the polymers and resins include but are not limited to those containing carboxyl moieties, such as acrylates and other carboxy polymers. Typically, water-insoluble polymers and resins have to be neutralized to about 90% of their carboxyl moieties to make them water soluble for the purpose of formulating products in aqueous solution and for the purpose of making products which have good non-build-up properties, i.e., can be easily washed off the hair after use. However, when used with the compositions of the present invention, little or no neutralization is needed to dissolve these polymers/resins. In part, an unneutralized or partially neutralized water-insoluble polymer or resin is solubilized because it is neutralized by the amphoteric surfactant contained in the presently claimed delivery system, but the amphoteric surfactant acting alone will not solubilize the polymer or resin in water and allow the pH to be acidic. As discussed with reference to the Gerstein patent above, if the polymer or resin is neutralized by the amphoteric surfactant alone, when one attempts to acidify the solution to prepare a hair care composition with acidic pH, as is desirable, the carboxyl moieties of the polymer or resin becomes unneutralized and precipitation occurs. It is the combination of the organic phospholipid, the nonionic surfactant, and the amphoteric surfactant of the present invention which achieves the solubility of the water-insoluble polymers or resins.

As for latexes, they generally have been used in cosmetics in an unneutralized form since they are used for their milky (insoluble) appearance. In the context of the present invention, however, water-insoluble latexes are neutralized to an alkaline pH and dissolve, producing a clear solution. To the best of the inventors' knowledge, neutralized latexes have not previously been used in cosmetic compositions.

In the case of the non-neutralized or partially-neutralized polymers or resins, where such substances are applied to the hair or skin from an alcoholic or aqueous/alcoholic system, their washability from the hair leaves a great deal to be desired. In contrast, where such polymers or resins are applied in a delivery system comprising at least one organic phospholipid; at least one amphoteric surfactant; and at least one nonionic surfactant, wherein the nonionic surfactant is present in an amount equal to or greater than the amount of the organic phospholipid, the polymers or resins can easily be rinsed off from the hair (no build-up) while providing strong hold for curls, if curls are what is desired.

The following are examples of polymers that can be incorporated into the delivery system of the present invention. The list is not intended to be limiting:

AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylatelt-butyl acrylamide).

Unneutralized or partially neutralized water-insoluble latexes have been used as film-formers in various applications. The following are latexes that can be incorporated into the delivery system of the present invention:

AMERHOLD DR-25 from Amerchol (acrylic acidimethacrylic acid/acrylates/meth acrylates), LUVIMER 36D from BASF (ethyl acrylatelt-butyl acrylatelmethacrylic acid), and ACUDYNE 258 from Rohm & Haas (acrylic acid/methacrylic acid/acrylates/methacrylates/hydroxy ester acrylates).

Up to 60% by weight of each of these polymers/resins/latexes were dissolved in 35% phospholipid/amphoteric surfactant/nonionic surfactant solutions where the phospholipid was lecithin and the ratio of lecithin:amphoteric:nonionic was 1:1.2:4. All the solutions were clear, indefinitely dilutable with water without precipitation and stable after 2 months on the shelf.

The aqueous phase of the inventive delivery system can contain additional ingredients such as anionic surfactants, organic salts, inorganic salts, proteins, hair dyes, water-soluble polymers, quaternaty ammonium compounds, complex and simple carbohydrates, amino acids, preservatives and fragrances.

If the inventive system is to be used in concentrated form, i.e., with about 5% by weight of the organic phospholipid and 1% of added water-insoluble ingredient, the composition preferably has a pH ranging from 4–12 for maximum stability and clarity. The more concentrated the solution, the better the delivery.

If this blend is diluted with water or the blend is used as an ingredient in another composition, then the pH has a broader range, i.e., preferably ranges from 2–12, and a wider variety of additives can be included in the solution. When water is added to a concentrated LAN, it may appear to form a cloudy solution at first if a large amount of water is added at once. The LAN will eventually go into solution, however, and become clear or at least clearer. The time to clear decreases as the LAN ratio increases. Once the organized structure of the LAN forms, the addition of more water does not affect clarity. These dilute blends are still very effective in delivering water-insoluble ingredients. The blends can be freeze-dried to hygroscopic solids that redissolve into water. Encapsulation of such solids so that they do not pick up and retain excess moisture is also contemplated. Such encapsulated solids can have desirable storage properties and would be easy to dissolve into water at various dilutions. Understandably, the need for dilution varies depending on the water-insoluble material to be employed.

Another embodiment of the present invention is drawn to a process for preparing the aqueous system of the present invention. This process comprises: (a) combining the following ingredients to obtain a mixture: at least one organic phospholipid capable of forming bilayers in aqueous solution, at least one nonionic surfactant, and at least one amphoteric surfactant, where the nonionic surfactant is present in an amount by weight equal to or greater than the amount of the organic phospholipid, (b) heating the mixture obtained in step (a), and (c) adding an aqueous solution to the heated mixture to obtain the desired carrier system. Water-insoluble ingredients may be added in step (a). Preferably the carrier system obtained can cany a high load (i.e., 50% is considered a high load) of the organic phospholipid/water-insoluble ingredient. The mixture is preferably heated at a temperature of 65° C. to 85° C., depending on the melting points of the solid surfactants.

More specifically, the preparation of the carrier system of the present invention may be carried out as follows. Lecithin (L) is dispersed in water. The water-insoluble material is combined with nonionic surfactant(s) (N) at appropriate ratios and added to the lecithin/water dispersion. An amnphoteric surfactant (A) is added and the mixture is heated, preferably to a temperature of from 75° C. to 85° C. The combination of these ingredients results in a solution which is clear to slightly hazy and is referred to as the "LAN," which can then be used as a "raw material" to make finished products.

Alternatively, lecithin, amphoteric surfactant(s) and nonionic surfactant(s) can be weighed to appropriate ratios and heated to 70° C. with stirring. Water is then added q.s. at the same temperature. Another alternative method of preparation comprises adding the water-insoluble ingredient with mixing after solutions have cooled. This last alternative method helps protect heat-sensitive water-insoluble ingredients.

The resulting compositions may vary from clear to slightly hazy and are infinitely dilutable with water. The slight haze can be overcome by adjusting the ratio of lecithin to the surfactants, adjusting pH, or reducing concentrations of water-insoluble ingredients.

In another embodiment, the present invention is drawn to a method for treating keratinous substances such as, but not limited to, hair, skin, or eyelashes. First an aqueous solution is prepared containing at least one organic phospholipid capable of forming bilayers in aqueous solution; at least one amphoteric surfactant; at least one nonionic surfactant present in an amount by weight equal to or greater than the amount of the phospholipid; and at least one water-insoluble ingredient. The phospholipid, amphoteric surfactant, and nonionic surfactant are present in a combined amount sufficient to allow the water-insoluble ingredient to be incorporated into the aqueous solution. The aqueous solution is then applied to the keratinous substances. The term treating in the context of this invention includes, but is not limited to, shampooing, conditioning, dyeing, bleaching, permanent waving, relaxing, setting, moisturizing, and making-up, for example, applying mascara or foundation.

As mentioned previously, the composition and carrier system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

With respect to hair products, the carrier system of the present invention can be used to formulate hair products, e.g., for normal hair, color-treated hair, dry hair, fine hair, and damaged hair. For each type of hair, the LAN can be used to create a regimen comprising shampoo, conditioner, and deep treatment, (i.e., deep conditioner). LAN compositions used for these products preferably contain lecithin (L), at least one amphoteric surfactant (A), such as disodium cocoamphodipropionate, and at least one nonionic surfactant (N), e.g., a blend of Oleth-10 and PPG-5-Ceteth-20. Additional nonionic, amphoteric, and also anionic surfactants can be added. The LAN compositions may further contain at least one water-insoluble ingredient (also referred to as a bydrophobe) such as olive, mineral, or other oils, octyl salicylate, Vitamin E (Tocopherol), octyl methoxycinnamate, and ceramides including 2-oleamido-1, 3-octadecanediol.

In general, the concentration of the LAN is increased within each regimen from shampoo to conditioner to deep treatment. Thus, the deep treatment formulations have the most concentrated hydrophobe-carrying LAN.

The LAN systems of the invention can be further associated, in the hair products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN and enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN is treated as a water-insoluble, particularly a lipophilic, ingredient itself.

Other ingredients in the LAN hair care compositions may include cationic polymers, such as polyquaternium 4, polyquaternium 6, polyquaternium 7, polyquaternium 10, polyquaternium 11, polyquatemium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffms, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

The invention will be fiurther clarified by the following examples, which are intended to be illustrative of the invention, but not limiting thereof.

EXAMPLES

Example 1

Determining Solubility Parameters in Mixture of Surfactants 5 g lecithin was dissolved in mixtures of MIRANOL C2M-SF Conc. (amphoteric surfactant) and ARLASOLVE 200 (Iso-Ceteth-20, nonionic surfactant). The water-insoluble (lipophilic) ingredient was olive oil. The results are shown in Tables 1 and 2 below.

TABLE 1

Optimizing Ratios of LAN Containing Olive Oil

| | Olive Oil/Lecithin Ratio (LOAD) | | | | | |
|---|---|---|---|---|---|---|
| | 0.2 | 0.3 | 0.4 | 0.5 | 0.6 | 1 |
| 1:1.2:2 LAN | clear | hazy | cloudy | cloudy | cloudy | cloudy |
| 1:1.2:3 LAN | clear | cloudy | cloudy | cloudy | cloudy | cloudy |
| 1:1.6:4 LAN | clear | clear | clear | clear | clear | cloudy |
| 1:2.0:5 LAN | clear | clear | clear | clear | clear | cloudy |

In Table 1, lecithin was fixed at 5 g, and various ratios of the LAN were studied as a function of load from 20 to 100%. (Load equals weight of added lipophile divided by weight of lecithin). At the lowest ratios of surfactants to lecithin, only a 20% load was achieved. In other words, for the ratio 1:1.2:2, the LAN solution was clear only at 0.2 or 20% load. As the ratio of surfactants to lecithin increased, however, the organized structure broke down. Thus, even though the LANs with bigger ratios of surfactants to lecithin theoretically can carry more lipophile, optimum results are achieved with a maximum of lecithin to a minimum of surfactant. The results show that a ratio of 1:1.2:2 gave a clear, dilutable mixture with olive oil.

TABLE 2

Optimizing the Amount of Nonionic and Amphoteric Surfactants

| ALCOLEC F100 (LECITHIN) | MIRANOL C2M-SF Conc. (AMPHOTERIC) | ARLASOLVE 200 (NONIONIC) | CLARITY | RATIO |
|---|---|---|---|---|
| 5 g | 10 g | 10 g | cloudy | 1:0.8:2 |
| 5 g | 10 g | 8 g | cloudy | 1:0.8:1.6 |
| 5 g | 15 g | 15 g | clear | 1:1.2:3 |
| S g | 15 g | 10 g | clear | 1:1.2:2 * |
| 5 g | 15 g | 5 g | cloudy | 1:1.2:1 |
| 5 g | 15 g | 3 g | cloudy | 1:1.2:0.6 |
| 5 g | 15 g | 8 g | cloudy | 1:1.2:1.6 |
| 5 g | 12 g | 10 g | cloudy | 1:0.96:2 |
| 5 g | 12 g | 8 g | cloudy | 1:0.96:1.6 |
| 5 g | 13 g | 9 g | cloudy | 1:1.04:1.8 |

* optimum ratio

Table 2 does not consider lipophilic load. The amounts of amphoteric and nonionic surfactants thus varied over a wider range of concentrations around the pair of points that are clear at 20% load in Table 1 (1:1.2:2) and (1:1.2:3). The table shows that the LAN ratio made a difference in the clarity of the solution. When the amount of the nonionic surfactant was increased, the solutions remained clear, but when the amount was decreased, the solutions became cloudy. The ratio of amphoteric to nonionic surfactant is maintained at a certain level for optimum results to be obtained but the total concentration of surfactants plays a role as well. For instance, when the ratio of amphoteric surfactant to nonionic surfactant was maintained at 1.2:2 and the total surfactant concentration was decreased relative to lecithin (i.e., from 1:1.2:2 to 1:0.96:1.6, which is the same ratio but different relative concentrations), the result was a cloudy solution. In this case, increasing the nonionic to 2.0, for example, did not clarify the mixture at this weight of lecithin.

The dilutability of solutions above the ratio of 1:0.8:2 (5 g:10 g:10 g) was infinite, though at that ratio the solutions were not quite clear. At a LAN ratio of 1:1.2:2, the solution was generally both clear and infinitely dilutable.

Example 2

Study of Solubility of Lipophilic Ingredients

The solubility of 2-oleamido-1,3-octadecanediol (a ceramide) and olive oil, lipophilic ingredients often used in hair care products, was evaluated in a mixture comprising 5 g lecithin and varying amounts of MSRANOL C2M-SF Conc. and ARLASOLVE 200. Both 2-oleamido-1,3-octadecanediol and olive oil, at the 1% level, formed a clear, stable lecithin solution with 15% (15 g) MIRANOL and 10% (10 g) ARLASOLVE. Thus, the lipophiles were solubilized best with a LAN ratio of 1:1.2:2.

Example 3

Study of HLB Values

Using different ratios of the nonionic surfactants BRIJ 72 (HLB 4.9) and BRIJ 700 (HLB 18.8), an HLB range from 5 to 18 was obtained. Only the even HLB values were studied. The formulations tested contained 5% ALCOLEC S, 15% MIRANOL C2M-SF Conc, and 15% nonionics (LAN ratio 1:1.2:3) with different HLB's. Surprisingly, none of the HLB values investigated provided clear solutions. In each case, thick gels were formed instead of solutions. See Table 3.

TABLE 3

HLB Systems (q.s. to 100 g water)

| ALCOLEC F100 (LECITHIN) | MIRANOL C2M-SF Conc. (AMPHOTERIC SURFACTANT) | NONIONIC SURFACTANT | OTHER INGRED | CLARITY | STABILITY |
|---|---|---|---|---|---|
| 5 g | 15 g | 13.82 g BRIJ 72 + 1.18 g BRIJ 700 (HLB 6) | — | very cloudy | — |
| 5 g | 15 g | 11.66 g BRIJ 72 + 3.34 g BRIJ 700 (HLB 8) | — | verycloudy | — |
| 5 g | 15 g | 9.5 g BRIJ 72 + 5.5 g BRIJ 700 (HLB 10) | — | very cloudy | — |
| 5 g | 15 g | 7.34 g BRIJ 72 + 7.66 g BRIJ 700 (HLB 12) | — | very cloudy | — |
| 5 g | 15 g | 5.18 g BRIJ 72 + 9.82 g BRIJ 700 (HLB 14) | — | very cloudy | — |

TABLE 3-continued

HLB Systems (q.s. to 100 g water)

| ALCOLEC F100 (LECITHIN) | MIRANOL C2M-SF Conc. (AMPHOTERIC SURFACTANT) | NONIONIC SURFACTANT | OTHER INGRED | CLARITY | STABILITY |
|---|---|---|---|---|---|
| 5 g | 15 g | 3.02 g BRIJ 72 + 11.98 g BRIJ 700 (HLB 16) | — | very cloudy | — |
| 5 g | 15 g | 0.86 g BRIJ 72 + 14.14 g BRIJ 700 (HLB 18) | — | very cloudy | — |

* BRIJ 72 = Steareth-2 HLB 4.9
* BRIJ 700 = Steareth-100 HLB 18.8

Example 4
Study of Solubility and Effectiveness of Dyes in the LAN

Solubility and effectiveness of dyes used in combination with the LAN were studied. The LAN provides three novel and surprising aspects to hair coloring/dyeing preparations in particular: (1) The LAN obviates the need for classical cosolvents typically included in hair coloring compositions such as ethanol, alkyl polyols, or propylene glycol, which serve to help solubilize dyestuffs into the color base; (2) No quaternized arnine compounds are needed to effect conditioning of the hair when the LAN is used; and (3) No nitrogen blanketing of the hair color composition is necessary during the compounding or storage of these compositions.

| Dye Composition 1 | |
|---|---|
| Deionized water | 61.4 g |
| Sodium sulfite | 1.0 g [antioxidant] |
| Isoascorbic acid | 0.8 g [antioxidant] |
| para-phenylenediamine | 0.8 g |
| p-amino-ortho-cresol | 0.15 g |
| meta-aminophenol | 0.3 g |
| para-aminophenol | 0.5 g |
| 2,4-diaminophenoxyethanol | 0.05 g |

The deionized water at 70° C. was added to a glass beaker, followed by the rest of the above ingredients. In another beaker, 5 g soy lecithin, 15 g MIRANOL C2M-SF Conc. (disodium cocoamphodipropionate), and 15 g ARLA-SOLVE 200 (iso-ceteth-20) (the LAN, in a ratio of 1:1.2:3) were heated to 70° C. and added to the aqueous phase with stirring. The pH was adjusted by adding aliquots of ammonium hydroxide to a pH of 8.4.

The resulting clear, pale amber hair color composition was stored for 5 weeks in a glass bottle. No nitrogen blanket was used. No crystallization occurred. No darkening of the solution occurred either.

A 10 g portion of the hair color composition was added to a plastic bowl and mixed with an equal volume of 20 vol hydrogen peroxide and then applied to level 6 natural brown hair, also containing 25% grey hair, for 20 minutes at ambient temperature. After 20 minutes, the hair was rinsed under running tap water for 10 minutes, dried with a commercial hair dryer to give L=19.11, a=0.82, b=−0.03.

L, a, and b are defined as follows. L indicates the lightness or darkness of the color value. The higher the L, therefore, the lighter the hair, and the more fading that has occurred. When L is 0, the hair is black, and when L is 100, the hair is white. −a and +a represent changes in color tone from green to red. −b and +b represent the changes in color tone from blue to yellow. In the present example, the hair color overall decreased to a medium brown tone of level 4 depth.

Dye Composition 2

Dye Composition 1 was prepared except that the antioxidant was 1.8 g isoascorbic acid instead of isoascorbic acid plus sodium sulfite. The resulting clear, pale amber hair color composition was stored for 5 weeks in a glass bottle. No nitrogen blanket was used. No crystallization occurred. No darkening of the solution occurred. The composition was applied to the hair as above, with the following results: L=22.11, a=0.70, b=−0.07. The hair color overall decreased to a brown tone of level 5 depth.

Dye Composition 3

Dye composition 1 was prepared, except that the pH was adjusted to 10. The resulting clear, pale amber hair color composition was stored for 5 weeks in a glass bottle. No nitrogen blanket was used. No crystallization occurred. No darkening of the solution occurred. The composition was applied to hair as above, with the following results: L=21.32, a=2.60, b=1.51. The hair color overall decreased to a brown tone of level 5 depth with red/gold tones.

Dye Composition 4

Dye composition 2 was prepared except that the pH was adjusted to 10. The resulting clear, pale amber hair color composition was stored for 5 weeks in a glass bottle. No nitrogen blanket was used. No crystallization occurred. No darkening of the solution occurred. The composition was applied to hair as above, with the following results: L=21.66, a=2.77, b=1.46. The hair color overall decreased to a brown tone of level 5 depth with red/gold tones.

Dye Composition 5

In a beaker, 5 g soy lecithin, 15 g MIRANOL C2M-SF Conc. (disodium cocoamphodipropionate), and 15 g ARLA-SOLVE 200 (Iso-Ceteth-20) (the LAN, in a ratio of 1:1.2:3) were heated to 70° C. Next, 0.8 g para-phenylenediamine, 0.15 g p-amino-ortho-cresol, 0.3 g meta-aminophenol, 0.5 g para-aminophenol, and 0.05 g 2,4-diaminophenoxyethanol were added to the melted composition with stirring. The stirred mixture was then added with stirring to 61.4 g deionized water at 70° C. containing 1.8 g isoascorbic acid and 0.8 g sodium sulfite. The pH was adjusted by adding aliquots of ammonium hydroxide to a pH of 10.

To a 40 g portion of the above composition was added 4 g of steareth-10 allyl ether/acrylates copolymer. The resulting clear pale amber gel was stored in a glass bottle for 5 weeks. No nitrogen blanket was used. No crystallization occurred. No darkening of the solution occurred.

As in dye composition 1, a 10 g portion of the hair color composition was added to a plastic bowl and mixed with an equal volume of 20 vol hydrogen peroxide and then applied to level 6 natural brown hair, containing 25% grey hair, for 20 minutes at ambient temperature. After 20 minutes, the hair was rinsed under running tap water for 10 minutes, dried with a commercial hair dryer to give L=20.69, a=1.72, b=0.86. The hair color overall decreased to a brown tone of level 5 depth with red/gold tones.

Dye compositions 1–5, formulated with the LAN, left the hair soft and conditioned and were stable solutions, lasting 5 weeks in storage before being used, and lasting much longer after that. LAN compositions containing added lipophiles have been stored for over 3 months at 45° C., yielding a predicted shelf life of 3 years at room temperature. Such LAN-containing solutions obviate the need for added co-solvents in such compositions.

Example 5
Study of Solubility of Lipophilic Ingredients in LANs of Varying pH Concentrated LAN solutions containing various lipophilic ingredients were studied at pH values ranging from 3 to 12. The lecithin was present at 5%, and the lipophilic ingredient was present in an amount of 1%. The LAN itself and the LAN plus a lipophile were cloudy at pH 3–5. At pH 6, the LAN itself was clear. At pH 11 and 12, all the solutions were clear. See Table 4.

TABLE 4

PROPERTIES OF CONCENTRATED LAN SOLUTIONS
CONTAINING LIPOPHILIC INGREDIENTS
(1:1.3:3 LAN ratio, 5% lecithin, 1% lipophilic ingredients)

• = CLOUDY   o = CLEAR

| Ingredient | pH 3 | pH 4 | pH 5 | pH 6 | pH 7 | pH 8 | pH 9 | pH 10 | pH 11 | pH 12 |
|---|---|---|---|---|---|---|---|---|---|---|
| LAN | • | • | • | o | o | o | • | o | o | o |
| + olive oil | • | • | • | • | o | o | • | o | o | o |
| +octyl methoxy cinnamate | • | • | • | • | • | • | • | o | o | o |
| +tocopherol | • | • | • | • | • | • | • | o | o | o |
| +octylcrylene | • | • | • | • | • | • | • | • | o | o |
| +Ceramide | • | • | • | • | • | • | • | • | o | o |

(Shaded areas indicate non-adjusted pH)

The table shows that concentrated LAN solutions are preferably more alkaline to be clear. Thus, the solutions at pH 10–12 had the best results. One of ordinary skill in the art would know that at different LAN ratios or concentrations, various degrees of clarity could be obtained.

Example 6
Preparation of Silicone/LAN Combinations

Silicones are highly desirable ingredients to enhance shine and softness but are difficult to formulate because of their inherent insolubility in water and alcohol. The silicones, phenyl trimethicone (A) and laurylmethicone copolyol (B), were formulated into LAN serums to yield clear, dilutable solutions. The nonionic surfactants were PPG-5-Ceteth-20, Oleth-10, and also decyl glucoside. The aiphoteric surfactant was disodium cocoamphodipropionate (MIRANOL C2M-SF Conc.).

| Ingredient | Amount in wt % A | B |
|---|---|---|
| Silicone | 2.0 | 2.0 |
| Lecithin | 4.0 | 4.0 |
| PPG-5-Ceteth-20 | 14.0 | — |
| Oleth-10 | — | 15.0 |
| Decyl glucoside | 15.0 | 10.0 |
| Disodium cocoamphodipropionate | 19.0 | 1.0 |
| Water | q.s. | q.s. |
| pH adjusted to 6.0–6.5 with phosphoric acid | | |

A: Load = 50% LAN ratio = 1:1.9:7.25
B: Load = 50% LAN ratio = 1:0.1:6.25

These LAN/silicone combinations could then be used to easily incorporate the silicone into shampoos, conditioners, and other formulations.

Example 7
Preparation of a Clear Shampoo for Color-Treated Hair

The following clear shampoo was formulated. It contained a LAN carrying sunscreens and Vitamin E. All ingredient amounts are shown in weight percent.

| The LAN* | 0.100% of the following LAN composition: |
|---|---|
| lecithin | 4.00% |
| disodium cocoamphodipropionate (amphoteric surfactant) | 19.00% |
| PPG-5-Ceteth-20 (nonionic surfactant) | 14.00% |
| Oleth-10 (nonionic surfactant) | 9.00% |
| methyl paraben | 0.20% |
| ethyl paraben | 0.10% |
| disodium EDTA | 0.10% |
| phenoxyethanol | 0.50% |
| phosphoric acid 85% (pH adjuster) | 1.40% |
| water | 49.70% |
| Vitamin E (tocopherol) | 1.00% |
| octyl salicylate (sunscreen) | 1.00% |

| In a shampoo base of: | |
|---|---|
| sodium laureth sulfate (anionic surfactant) | 25.000% |

-continued

In a shampoo base of:

| | |
|---|---|
| polyquaternium 10 (polymer) | 0.100% |
| PPG-5-Ceteth-10-phosphate (emollient) | 0.500% |
| disodium cocoamphodipropionate (amphoteric surfactant) | 5.000% |
| cocamidopropyl betaine (amphoteric surfactants) | 8.00% |
| octyl methoxy cinnamate (sunscreen) | 0.100% |
| phosphoric acid (85%) | 0.800% |
| sodium chloride | 0.500% |
| fragrance | 0.500% |
| preservatives selected from phenoxyethanol, methylparaben, ethylparaben, and disodium EDTA | 0.800% |
| proteins and amino acids selected from taurine, arginine hydrochloride, lauryldimonium hydroxypropyl hydrolyzed soy protein, and hydrolyzed soy protein with wheat amino acid | 0.400% |
| trehalose (humectant) | 0.001% |
| water | q.s. to 100 |

Example 8
Preparation of a Conditioner for Color-Treated Hair

The following emulsified cream treatment containing cationic conditioners, silicones, cationic polymers, sunscreens and Vitamin E, was formulated: The LAN . . . same LAN formulation as set forth in example 7 . . . 0.500%

In a conditioner base of:

| | |
|---|---|
| glyceryl stearate and PEG-100 stearate (nonionic emulsifiers) | 5.000% |
| quaternium 27 | 4.000% |
| hexadimethrine chloride (cationic) 0.5% and hydroxyethyl cellulose (cationic and cellulosic polymers) | 0.8% 1.300% |
| octyl methoxycinnamate (sunscreen) | 0.100% |
| dimethicone (silicone) | 2.000% |
| stearyl alcohol (emollient) | 5.000% |
| octyldodecanol (emollient) | 2.000% |
| sodium citrate | 0.150% |
| fragrance | 0.500% |
| preservatives selected from phenoxyethanol, methylparaben, ethylparaben, propylparaben and disodium EDTA | 0.900% |
| proteins and amino acids selected from taurine, arginine hydrochloride, lauryldimonium hydroxypropyl hydrolyzed soy protein, and hydrolyzed soy protein with wheat amino acid | 0.400% |
| trehalose (humectant) | 0.001% |
| water | q.s. to 100 |

Example 9
Preparation of a Deep Treatment for Color-Treated Hair

The following viscous aqueous fluid containing cationic conditioners, silicones, cationic polymers (e.g., polyacrylamide), sunscreens and Vitamin E, was formulated: The LAN . . . same LAN formulation as set forth in example 7 . . . 20.000%

In a treatment base of:

| | |
|---|---|
| SEPIGEL 305 (polyacrylamide/$C_{13}$—$C_{14}$ isoparaffin/laureth 7, available from SEPPIC) | 2.000% |
| xanthan gum | 1.000% |
| behenamidopropyl PG-dimonium chloride (cationic conditioner) | 3.000% |
| cetrimonium chloride (cationic conditioner) | 3.000% |
| cyclomethicone and dimethicone | 3.000% |
| octyl methoxycinnamate (sunscreen) propylene glycol | 0.100% |
| fragrance | 0.500% |
| preservatives selected from phenoxyethanol, methylparaben, ethylparaben, and disodium EDTA | 0.800% |

-continued

In a treatment base of:

| | |
|---|---|
| proteins and amino acids selected from taurine, arginine hydrochloride, lauryldimonium hydroxypropyl hydrolyzed soy protein, and hydrolyzed soy protein with wheat amino acid | 1.210% |
| phosphoric acid 85% (pH adjuster) | 0.060% |
| trehalose (humectant) | 0.001% |
| water | q.s. to 100 |

Example 10
Color Retention Effects of Color Treatment Products Against Chlorine Water and Shampooing Dyed brown hair was treated with 5 ppm chlorine water during a regime of deep treatment, shampoo and conditioner formulated as described above for color-treated hair for 1 week (1 deep treatment, 4 shampoos and 4 conditioners). To obtain significant experimental data, an experiment was carried out in which 72 brown hair swatches were colored, followed by:

24 swatches treated with:
  Treatment (10 minutes/room temperature (RT), rinse)
  Shampoo (5 minutes/RT, rinse)
  Conditioner (10 minutes/RT, rinse)

The shampoo and conditioner treatment was repeated 3 more times, representing one week of product use, and the chlorine treatments (5 ppm chlorine water for 30 minutes at room temperature/rinse) were done after the 1st and the 4th cycle:

24 swatches treated with chlorine water during the regimen for color-treated hair as described above but without Arginine, Taurine, Proteins, LAN, Vitamin E, sunscreens in the products 24 swatches treated with chlorine water during the regimen for color-treated hair as described above but with water instead of the described hair products The table below shows that frequent use of the products for color-treated hair protects the color from fading against chlorine water and shampoos. L indicates how much the color has faded. The higher the L value, the lighter the color, i.e., the more fading has occurred. The effects of the LAN and additional ingredients such as the proteins are also apparent.

TABLE 5

MEAN L VALUES

| | Control | After 1 week of shampooing/ chlorine water treatment | Change in L | % change in L |
|---|---|---|---|---|
| water only | 24.61 | 28.09 | 3.48 | 14.14% |
| regimen of invention | 23.96 | 25.61 | 1.65 | 6.89% |
| regimen w/o LAN, proteins, amino acids, vitamin E, or sunscreens | 24.74 | 27.46 | 2.72 | 10.89% |

It is clear that the smallest change in L, i.e, the least fading, occurred when the LAN containing regimen of the invention was used.

Example 11
Solubility of AMPHOMER LV-71 in LAN v. Non-LAN Solutions

The following four solutions were prepared according to Table 6 below.

Solution A: A 1:1.2:5 aqueous LAN solution containing the water-insoluble polymer AMPHOMER LV 71.
Solution B: A 1:1.2:5 aqueous LAN solution containing AMPHOMER LV 71 and sodium lauryl ether sulfate (SLES), an anionic surfactant.
Solution C: An aqueous solution of AMPHOMER LV 71 in an amphoteric surfactant and an anionic surfactant. No lecithin and no nonionic surfactant were present. This solution was prepared according to Example 1 of U.S. Pat. No. 5,391,368 to Gerstein.
Solution D: An aqueous solution of AMPHOMER LV 71 in an amphoteric surfactant only. No lecithin or nonionic surfactant were present.

TABLE 6

|  | Solution A | Solution B | Solution C | Solution D |
|---|---|---|---|---|
| ALCOLEC F100 (Lecithin) | 2.67 | 2.67 | — | — |
| MIRANOL C2M-SFConc. (Amphoteric) | 8 | 8 | 8 | 8 |
| ARLASOLVE 200 (Nonionic) | 13.35 | 13.35 | — | — |
| AMPHOMER LV 71 (Polymer) | 3 | 3 | 3 | 3 |
| SLES (Anionic) | — | 50 | 50 | — |
| WATER | 72.98 | 22.98 | 39 | 89 |

The solutions A–D were acidified with 10% hydrochloric acid down to pH 3. The pH and the appearance of each solution after acidification to various pH levels are shown below:

TABLE 7

|  | Initial | | Appearance after acidification to pH: | | | | |
|---|---|---|---|---|---|---|---|
| Solution | pH | Appearance | 7 | 6 | 5 | 4 | 3 |
| A | 6.9 | clear | clear | clear | clear | clear | clear |
| B | 7.05 | clear | clear | clear | clear | clear | clear |
| C | 7.4 | clear | clear | clear | cloudy | cloudy | cloudy |
| D | 7.2 | clear | clear | hazy | cloudy | cloudy | cloudy |

It is evident from the results shown in Table 7 that solubilization of a water-insoluble polymer in an aqueous LAN solution (solutions A and B) is far superior to solubilization of the same polymer in a non-LAN solution (solutions C and D). Solutions A and B stayed clear from pH 7 down to pH 3, whereas solution C was cloudy from pH 5 down and solution D began to get hazy at pH 6. In other words, the water-insoluble polymer precipitates out of solution at acidic pH in the non-LAN systems.

Example 12
Solubility of other Water-insolubles in LAN v. Non-LAN Solutions

The same tests as in Example 11 were carried out with ULTRAHOLD STRONG, another water-insoluble polymer, and LUVIMER 36D, a water-insoluble latex. The components of Solutions 1–6 are set forth in Table 8 below.

TABLE 8

|  | Solution 1 | Solution 2 | Solution 3 | Solution 4 | Solution 5 | Solution 6 |
|---|---|---|---|---|---|---|
| ALCOLEC F100 | — | — | 2.67 | — | — | 2.67 |
| MIRANOL C2M-SF CONC | 8 | 8 | 8 | 8 | 8 | 8 |
| ARLASOLVE 200 | — | — | 13.35 | — | — | 13.35 |
| SLES | 50 | — | — | 50 | — | — |
| LUVIMER 36D | 8.12 | 8.12 | 8.12 | — | — | — |
| ULTRAHOLD STRONG | — | — | — | 3 | 3 | 3 |
| WATER | 33.88 | 83.88 | 67.86 | 39 | 89 | 72.98 |

Solutions 3 and 6 were LAN solutions, with LAN ratio 1:1.2:5. Solutions 1 and 4 contained an amphoteric and an anionic polymer, and Solutions 2 and 5 contained only an amphoteric polymer. The solutions were acidified with 10% hydrochloric acid down to pH 3. The pH and the appearance of each solution after acidification to various pH levels are shown below in Table 9.

TABLE 9

|  | Initial | | Appearance after acidification to pH: | | | | |
|---|---|---|---|---|---|---|---|
| Solution | pH | Appearance | 7 | 6 | 5 | 4 | 3 |
| 1 | 7.40 | clear | clear | cloudy | cloudy | cloudy | cloudy |
| 2 | 7.32 | clear | cloudy | cloudy | cloudy | cloudy | cloudy |
| 3 | 7.12 | clear | clear | clear | clear | clear | clear |
| 4 | 8.42 | cloudy | cloudy | cloudy | cloudy | cloudy | cloudy |
| 5 | 7.62 | cloudy | cloudy | cloudy | cloudy | cloudy | cloudy |
| 6 | 7.35 | clear | clear | clear | clear | clear | clear |

These results demonstrate, as in Example 11, that solubilization of a water-insoluble polymer or latex in an aqueous LAN solution is far superior to solubilization of the same polymer or latex in a non-LAN solution. LAN solutions 3 and 6 remained clear all the way down to pH 3, whereas solutions 4 and 5 were initially cloudy even before acidification, solution 1 was cloudy from pH 6 and solution 2 from pH 7.

Example 13

Determination of Load of Polymer/Latex that LAN Solution can Carry

LAN solutions containing a water-insoluble polymer or latex were prepared as set forth in Table 10. Solution E had a LAN ratio of 1:1.2:4 and contained 10% by weight of AMPHOMER. Solution F had a LAN ratio of 1:2:5 and contained 15% by weight of AMPHOMER. Solution G had a LAN ratio of 1:1.2:4 and contained 60% by weight of AMERHOLD DR-25 (latex).

TABLE 10

|  | Solution E | Solution F | Solution G |
|---|---|---|---|
| ALCOLEC F100 | 5 | 5 | 5 |
| MIRANOL C2M-SF CONC | 15 | 25 | 15 |
| ARLASOLVE 200 | 20 | 25 | 20 |
| WATER-INSOLUBLE POLYMER OR LATEX | AMPHOMER LV-71 10 | AMPHOMER LV-71 15 | AMERHOLD DR-25 60 |
| WATER | 50 | 30 | — |

Each of solutions E, F, and & were clear solutions. At amounts of polymer or latex over 60% by weight, the polymer or latex could still be dissolved in the LAN system but the solution became very viscous.

Example 14
Determination of Additional Load LAN/polmer System can Carry

LAN solutions containing 3% of AMPHOMER (water-insoluble polymer) as well as a silicone ingredient were prepared as set forth in Table 11. Solution H had a LAN ratio of 1:1.2:4 and contained 1% by weight of phenyltrimethicone. Solution I had a LAN ratio of 1:1.2:4 and contained 1% by weight of dimethicone.

TABLE 11

|  | Solution H | Solution I |
|---|---|---|
| ALCOLEC F100 | 5 | 5 |
| MIRANOL C2M-SF CONC | 15 | 15 |
| ARLASOLVE 200 | 20 | 20 |
| SILICONE COMPOUND | Phenyltrimethicone 1 | Dimethicone 1 |
| WATER-INSOLUBLE POLYMER | AMPHOMER LV-71 3 | AMPHOMER LV-71 3 |
| WATER | 56 | 30 |

Both solutions H and I were clear solutions. This demonstrates that the LAN system is effective in carrying water-insoluble ingredients as well as simultaneously carrying other ingredients. For example, LAN/polymer systems can also contain ceramides, sunscreens, oil, vitamins.

Example 15
Performance of LAN Solutions Containing Non-neutralized Polmers

A LAN carrier solution was prepared having the following ingredients:

| | |
|---|---|
| Lecithin (ALCOLEC F100) | 5 g |
| Amphoteric Surfactant (MIRANOL C2M-SF Conc.) | 15 g |
| Nonionic Surfactant (ARLASOLVE 200) | 15 g |
| Water-insoluble polymer (AMPHOMER LV-71) | 6 g |
| Water | q.s. 100 g |

The following series of solutions were obtained by diluting an appropriate amount of the LAN/6% AMPHOMER solution above to 100 g of water:

TABLE 12

|  | g LAN/6% polymer in 100 g water | ALCOLEC (Lecithin) | MIRANOL (Amphoteric Surfactant) | ARLASOLVE (Nonionic Surfactant) | AMPHOMER (Water-insol. polymer) | WATER |
|---|---|---|---|---|---|---|
| Dilution 1 | 2 | 0.1 | 0.3 | 0.4 | 0.12 | 99.08 |
| Dilution 2 | 6 | 0.3 | 0.9 | 1.2 | 0.36 | 97.24 |
| Dilution 3 | 10 | 0.5 | 1.5 | 2.0 | 0.6 | 95.40 |
| Dilution 4 | 20 | 1.0 | 3.0 | 4.0 | 1.2 | 90.8 |

The curl efficiency of hair treated with the above diluted solutions of the LAN/6% AMPHOMER is shown in FIG. 1. The data indicated that the performance of the diluted LAN/polymer solutions increased with the concentration of the non-neutralized AMPHOMER present.

Thus, the organic phospholipid, amphoteric surfactant and nonionic surfactant, which act in combination as an effective solvent for the unneutralized or partially neutralized water-insoluble polymer, resin, or latex, give better results/enhanced performance when diluted or when the percentage of LAN in solution is lower. Preferably, the percentage of LAN in solution is 35% or less, relative to the weight of the total composition. At percentages over 35%, the LAN acts as a plasticizer for the polymer, resin, or latex, thus reducing the hold desired for styling products. Of course, if the LAN is to be used in a product whose central purpose is not styling, such as a shampoo, dye composition, or relaxing composition, the percentage of LAN present can be higher without deleterious effects, and in fact a larger percentage of LAN may help in the complete incorporation of the polymer, resin, or latex in the non-styling product.

Example 16
Performance of LAN Solutions Containing Partially Neutralized Polymers To maximize the load of the polymers/resins that are soluble in a minimum amount of LAN in aqueous solution, the polymers/resins were partially neutralized. As discussed above, generally, water-insoluble polymers or resins are water soluble only when they are about 90% neutralized. Using the LAN makes it possible to solubilize polymers or resins which are neutralized to a much lesser degree, as illustrated by this example.

Two LAN carrier solutions were prepared by dissolving a total of 4% polymer/resin (2% AMPHOMER LV-71 and 2%

RESYN 28-2930) that were neutralized to 60% with aminomethylpropanol (AMP) in 1.2% and 0.8% LAN (1:1.2:4) solutions.

TABLE 13

|  | ALCOLEC | MIRANOL | ARLASOLVE | AMPHOMER | RESYN | AMP | WATER | % NEUTR |
|---|---|---|---|---|---|---|---|---|
| Solution 1 | 0.15 | 0.45 | 0.6 | 2 | 2 | 0.386 | 99.08 | 60% |
| Solution 2 | 0.10 | 0.30 | 0.4 | 2 | 2 | 0.386 | 97.24 | 60% |

Figure 2:
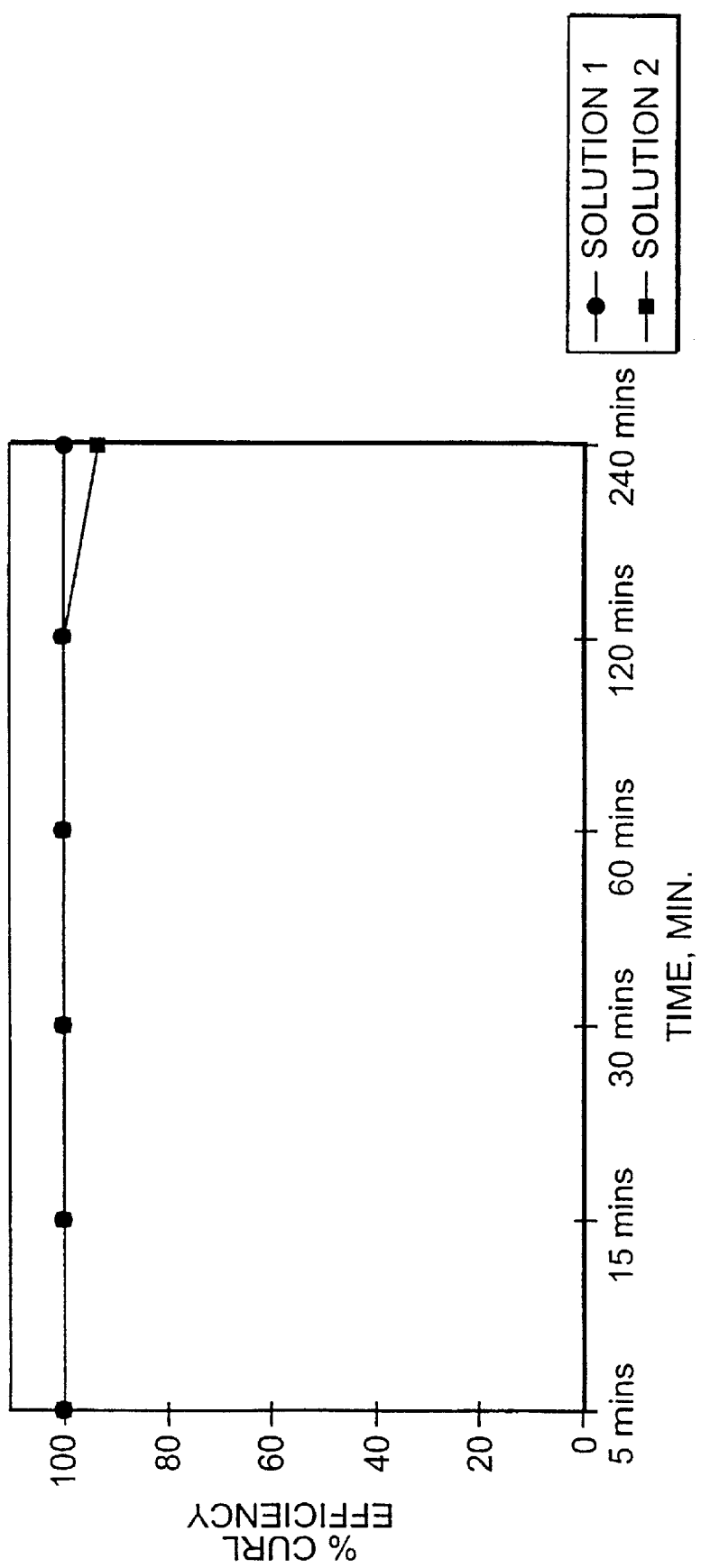

The performance of the above solutions in hair setting is shown in FIG. 2, which illustrates the exceptional curl retention of hair treated with the above solutions of LAN/partially neutralized polymer/resin at 95% after 4 hours.

Example 17
Effect of Degree of Neutralization on Hair Setting Performance

Four 0.8% LAN (1:1.2:4) solutions were prepared, each containing 1% of AMPHOMER LV-71 and being 20%, 40%, 60% and 80%, respectively, neutralized by AMP (aminomethylpropanol).

TABLE 14

|  | ALCOLEC | MIRANOL | ARLASOLVE | AMPHOMER | AMP | WATER | % NEUTRALIZ |
|---|---|---|---|---|---|---|---|
| Solution A | 0.1 | 0.3 | 0.4 | 1 | 0.043 | 98.157 | 20% |
| Solution B | 0.1 | 0.3 | 0.4 | 1 | 0.087 | 98.113 | 40% |
| Solution C | 0.1 | 0.3 | 0.4 | 1 | 0.131 | 98.069 | 60% |
| Solution D | 0.1 | 0.3 | 0.4 | 1 | 0.174 | 98.026 | 80% |

Figure 3:
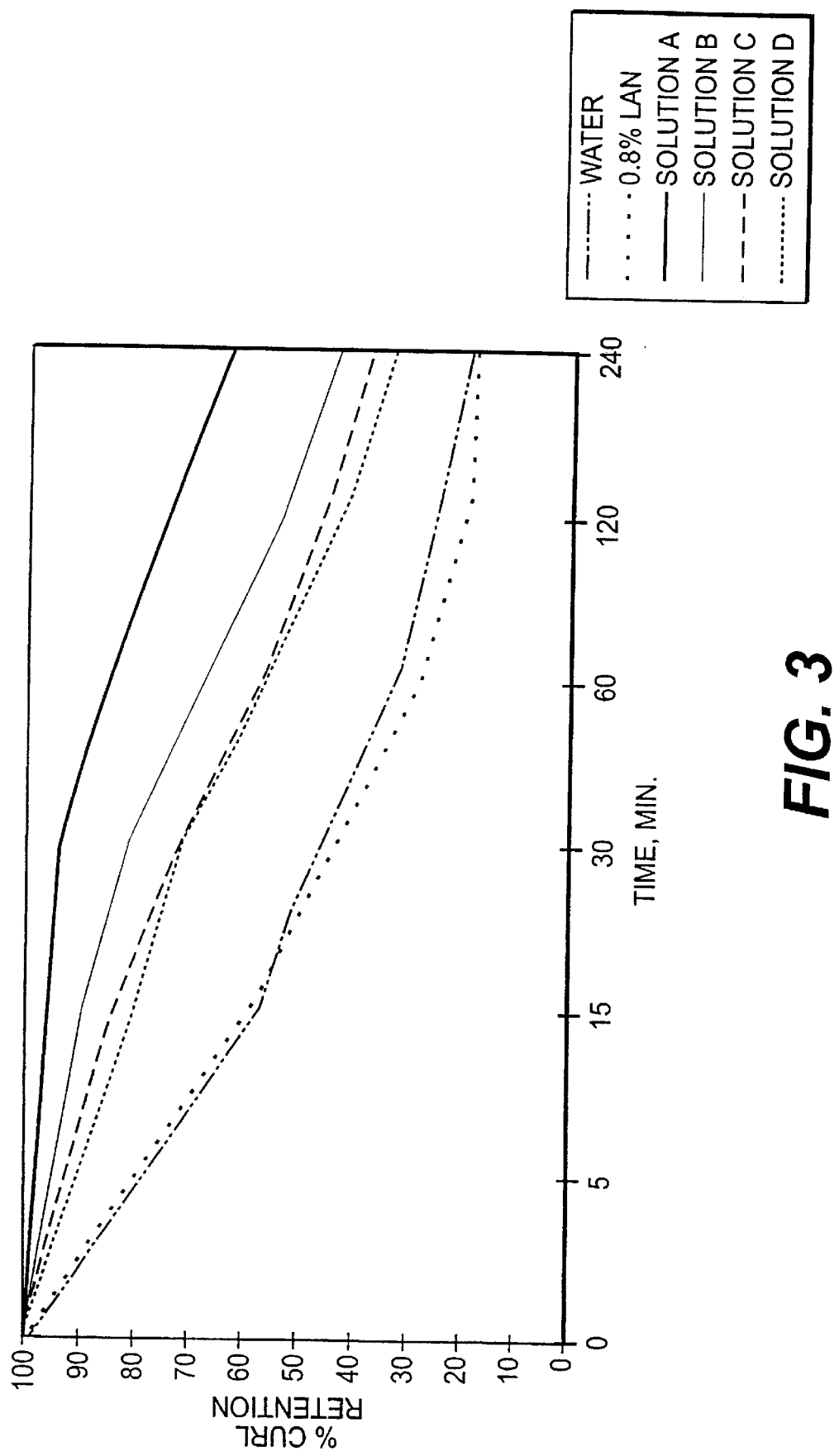

The curl retention of the above solutions A–D are shown in FIG. 3. The figure illustrates that the efficiency of LAN solutions containing partially neutralized polymers or resins is dependent on the degree of neutralization, i.e., the hair setting performance increased as the degree of neutralization decreased. In other words, the aqueous LAN systems are able to successfully incorporate water-insoluble high performance polymers/resins whereas previously such polymers/resins could be incorporated only into non-aqueous systems based on organic solvents.

Example 18
Performance of LAN Solutions Containing Partially Neutralized Polymers and Increasing Amounts of Polymer/resin: Curl Efficiency Five LAN carrier solutions were prepared. Each contained 0.8% LAN (ALCOLEC F100, MIRANOL C2M-SF Conc., and ARLASOLVE 200) and 0% to 4%, respectively, of a 60% neutralized water-insoluble polymer, AMPHOMER LV-7 1. See Table 15:

TABLE 15

|  | ALCOLEC | MIRANOL | ARLASOLVE | AMPHOMER | AMP | WATER |
|---|---|---|---|---|---|---|
| LAN | 0.1 | 0.3 | 0.4 | 0 | 0 | 99.2 |
| Solution A | 0.1 | 0.3 | 0.4 | 1 | 0.131 | 98.07 |
| Solution B | 0.1 | 0.3 | 0.4 | 2 | 0.262 | 96.94 |
| Solution C | 0.1 | 0.3 | 0.4 | 3 | 0.393 | 95.81 |
| Solution D | 0.1 | 0.3 | 0.4 | 4 | 0.524 | 94.68 |

Figure 4:
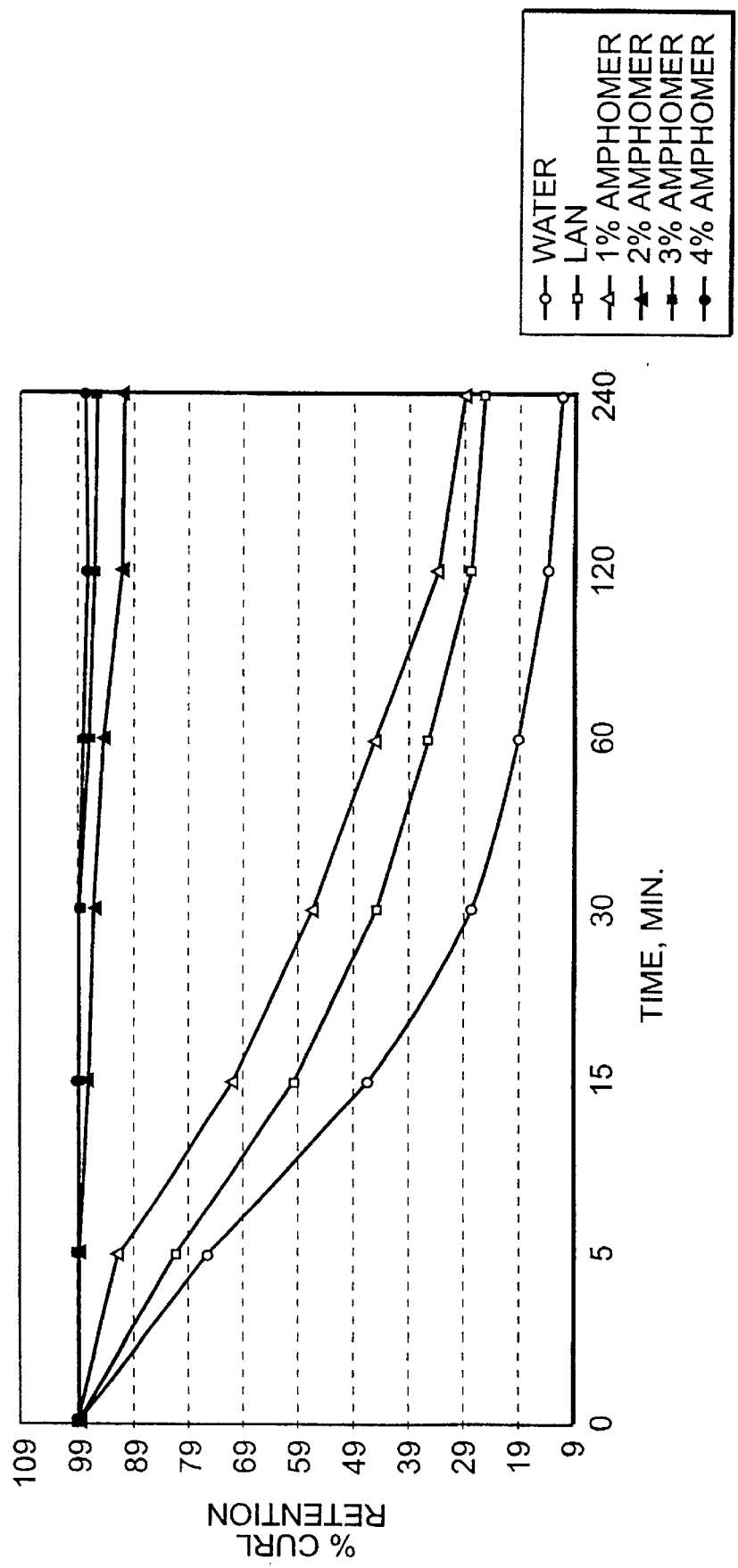

The compositions were compared for percent curl efficiency over a period of 4 hours. See FIG. 4, which shows that as the amount of styling polymer in the LAN solution increased from 0% to 4%, so did the curl retention, i.e., efficiency.

Example 19

Performance of LAN Solutions Containing Martially Neutralized Polymers and Increasing Amounts of Polymer/resin Five solutions were prepared. Solution 1 contained 4% LUVISKOL VA64, which is a water-soluble polyvinylpyrrolidone/vinyl acetate co-polymer from BASF, and 96% water. Solutions 2–5 were LAN/AMPHOMER solutions in which the LUVISKOL was gradually replaced with AMP as the amount of AMPHOMER increased. See Table 16:

TABLE 16

|  | ALCOLEC | MIRANOL | ARLASOLVE | AMPHOMER | AMP | LUVISKOL | WATER |
|---|---|---|---|---|---|---|---|
| Solution 1 | — | — | — | — | — | 4 | 96.00 |
| Solution 2 | 0.1 | 0.3 | 0.4 | 1 | 0.131 | 3 | 95.07 |
| Solution 3 | 0.1 | 0.3 | 0.4 | 2 | 0.262 | 2 | 94.93 |
| Solution 4 | 0.1 | 0.3 | 0.4 | 3 | 0.393 | 1 | 94.81 |
| Solution 5 | 0.1 | 0.3 | 0.4 | 4 | 0.524 | — | 94.68 |

Figure 5:
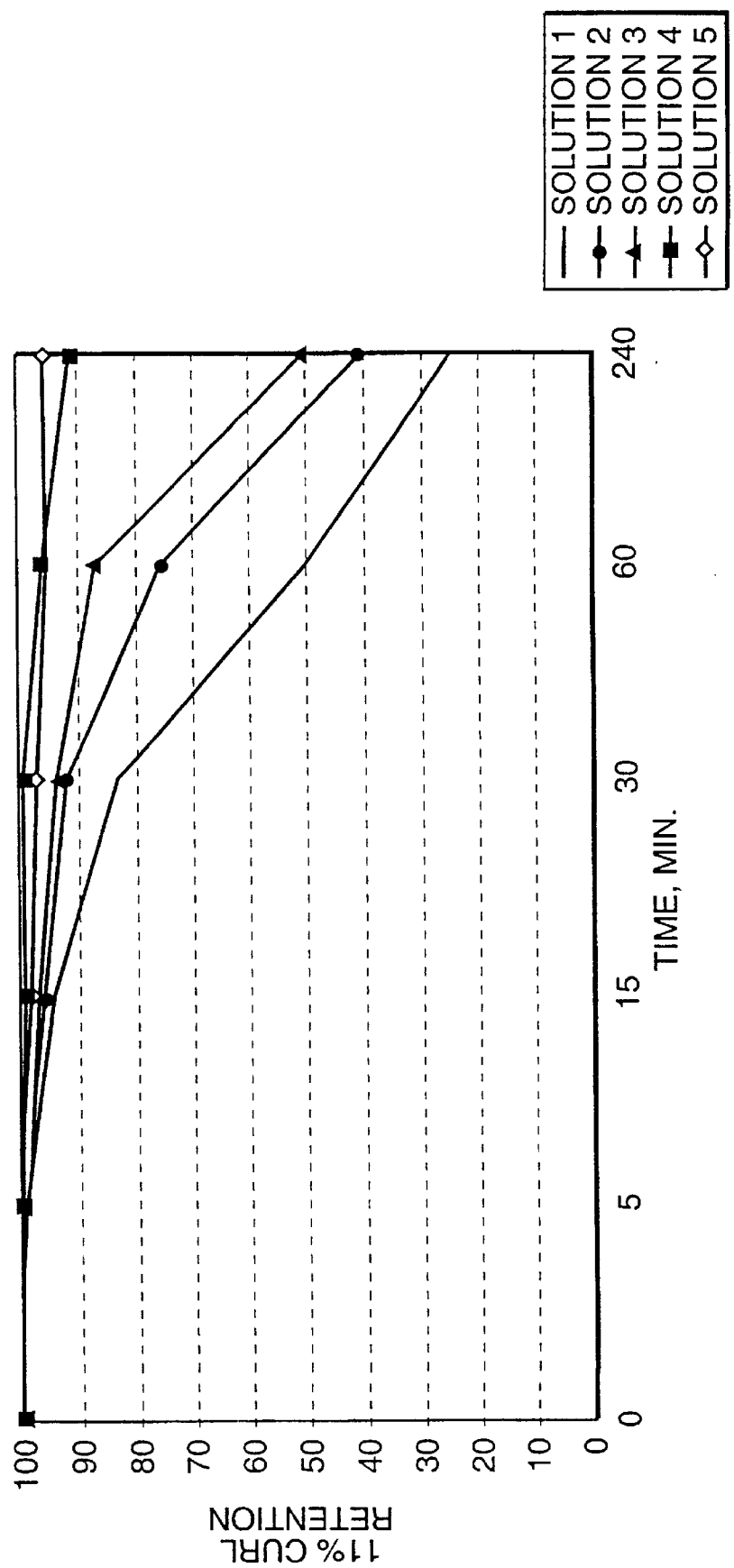

The compositions were compared for percent curl efficiency over a period of 4 hours. See FIG. 5, which shows that as the LAN/polymer solution replaced the conventional water soluble polymers/resins, the performance increased, i.e., the curl retention was excellent for Solutions 4 and 5, wherein there was little or no LlVISKOL.

Example 20
Improvement of Permanent Waving Efficieny

Three sets of 6 hair swatches (12 hair fibers, 13.8 cm each, per swatch) were wrapped around permanent waving rods, then saturated with the following solutions:

TABLE 17

|  | SOLUTION 1 (control) | SOLUTION 2 (LAN 1:1.2:4) | SOLUTION 3 (LAN + polymer) |
|---|---|---|---|
| Ammonium Thioglycolate (60%) (permanent wave lotion) | 11.67 | 11.67 | 11.67 |
| ALCOLEC F100 (Lecithin) | — | 0.0625 | 0.0625 |
| MIRANOL C2M-SF Conc. (Amphoteric) | — | 0.1875 | 0.1875 |
| ARLASOLVE 200 (Nonionic) | — | 0.25 | 0.25 |
| AMPHOMER LV-71 | — | — | 1 |
| Aminomethylpropanol (AMP) | — | — | 0.13 |
| Water | 88.33 | 87.83 | 86.7 |
| Ammonium Hydroxide |  | q.s. to pH 9.2 |  |

After 30 minutes at room temperature, the hair swatches (still on the rods) were thoroughly rinsed with water and blotted dry. They were then treated with a 2% hydrogen peroxide solution for 5 minutes at room temperature, rinsed thoroughly with water and blotted dry. The hair swatched were removed from the rods and their length measured. The following results were obtained:

TABLE 18

|  | Average Curl Length (cm) |
|---|---|
| Hair Treated with Solution 1 | 7.0 ± 0.62 |
| Hair Treated with Solution 2 | 7.4 ± 0.38 |
| Hair Treated with Solution 3 | 6.2 ± 0.45 |

As can be seen in Table 18, the hair treated with the reducing solution containing LAN/AMPHOMER displayed a better curl efficiency. The improvement is statistically significant at a 95% confidence level.

Example 21
Preparation of Clear Transparent Hydrogen Peroxide Gel

A series of clear taansparent gels made up of LAN/ Polymer that contained 3%, 6%, 9%, and 12% hydrogen peroxide at pH 3–4 were obtained. The polymer used in the gels was VISCOPHOBE DB-1000, an acryic acid latex from Union Carbide. A typical clear hydrogen peroxide/LAN/ VISCOPHOBE gel has the following formula:

| ALCOLEC F100 | 1 |
|---|---|
| MIRANOL C2M-SF CONC | 10 |
| ARLASOLVE 200 | 15 |
| VISCOPHOBE DB-1000 | 12 |
| Hydrogen Peroxide | 24 |
| Water | 38 |
| Phosphoric Acid | q.s. to pH 3 |

The viscosity of the gels can be adjusted by the amount of the VISCOPHOBE used in the formula. As shown below in Table 19, the hydrogen peroxide/LAN/VISCOPHOBE gels are efficient color developers when compared with PRO-OXIDE, a commercially available developer from RED-KEN.

TABLE 19

| Developer | L | a | b |
|---|---|---|---|
| Hair Color 1 |  |  |  |
| 20 vol. PRO-OXIDE | 29.65 | 20.93 | 13.35 |
| 20 vol. H$_2$O$_2$/1:4:16 LAN/12 VISCOPHOBE | 30.83 | 18.43 | 13.05 |
| 20 vol. H$_2$O$_2$/1:4:15 LAN/15 VISCOPHOBE | 33.32 | 19.31 | 15.12 |
| 20 vol. H$_2$O$_2$/1:4:25 LAN/15 VISCOPHOBE | 31.11 | 17.95 | 13.10 |
| Hair Color 2 |  |  |  |
| 20 vol. PRO-OXIDE | 24.25 | 6.12 | 5.29 |
| 20 vol. H$_2$O$_2$/1:4:16 LAN/12 VISCOPHOBE | 24.07 | 5.38 | 5.25 |

As shown in Table 19, the L value, which indicates the lightness or darkness of the color, increased for Hair Color 1 as compared to the PRO-OXIDE L value and decreased for Hair Color 2. In other words, this Table shows that hydrogen peroxide/LAN/VISCOPHOBE gel works as well or better than the known developer PRO-OXIDE. It is advantageous to use a gel as a developer since it is easier to control its application due to the reduced flow as compared to a liquid developer.

The hydrogen peroxide/LAN/VISCOPHOBE gels can also be used with a liquid aqueous color system to yield aqueous no-solvent color gels. When a clear hydrogen peroxide/LAN/VISCOPHOBE gel at pH 34 is mixed with an aqueous color system at pH 8 or higher in a 1:1 ratio, a thick color gel is obtained that can efficiently color the hair. As for the bleaching effects on hair, the hydrogen peroxide/ LAN/VISCCOPHOBE gels can be used to lift natural hair color at room temperature and show increased efficiency at higher temperatures.

Example 22
Mascara Formulation

A mascara composition is formulated from the following ingredients, including the LAN, which is present in a ratio of approximately 1:1.2:4 and in an amount of less than 1%:

(A)

| | |
|---|---|
| Water | 39.250 |
| PVP-K-30 (PVP/VA copolymer, GAF/BASF) | 1.000 |
| Butylene glycol | 2.000 |
| Hydroxyethylcellulose | 0.350 |
| Methyl paraben | 0.400 |
| Triethanolamine | 1.500 |
| Simethicone (MIRASIL SM from Rhodia Chimie) | 0.100 |
| KAMA KM 13 (Polysaccharide resin from Kama Int'l) | 4.000 |
| Iron oxide | 8.000 |
| Polymethyl methacrylate isopropyl titanium triisostearate | 2.000 |

(B)

| | |
|---|---|
| Beeswax | 4.300 |
| Glyceryl stearate | 4.000 |
| Paraffin | 2.500 |
| Carnauba wax | 3.100 |
| Stearic acid | 3.000 |
| Butylparaben | 0.050 |
| PVP/eicosene copolymer (GANEX V220, from ISP) | 1.500 |
| PERFORMA V103 Polymer (synthetic wax from New Phase) | 1.000 |

(C)

| | |
|---|---|
| Cyclopentasiloxane (DC 245 from Dow Corning) | 2.000 |
| Cyclopentasiloxane/Dimethiconol (DC 2-9071 from Dow Corning) | 3.000 |
| Silica | 1.000 |
| Polyethylene (MICROPOLY 524 from Presperse) | 2.000 |

(D)

| | | |
|---|---|---|
| Lecithin (ALCOLEC F100) | (L) | 0.133 |
| Disodium Cocoamphodipropionate (MIRANOL) | (A) | 0.400 |
| Isoceteth-20 (ARLASOLVE 200) | (N) | 0.530 |
| Octylacrylamide/acrylates/butylaminoethyl methacrylate copolymer (AMPHOMER LV-71) | | 0.160 |
| Methylparaben | | 0.005 |
| Ethylparaben | | 0.003 |
| Disodium EDTA | | 0.003 |
| Phenoxyethanol | | 0.013 |
| Water | | 1.403 |

(E)

| | |
|---|---|
| AVALURE UR450 (resin solution from B. F. Goodrich) | 10.000 |

(F)

| | |
|---|---|
| Imidazolidinyl urea | 0.300 |
| Water | 1.000 |

The procedure used to make the mascara composition was as follows, using a total of 100 g of material:

(A) 39.250 g water was heated to 60° C. and 1.000 g of PVP/VA copolymer was added. When the copolymer was dispersed, 2.000 g of butylene glycol and 0.350 g of hydroxyethylcellulose, which were pre-mixed, were added and the entire mixture dispersed using a Homomixer. When dispersed, 0.400 g methyl paraben, 1.500 g triethanolamine, 0.100 g MIRASIL SM (simethicone), and 4.000 g KAMA KM 13 (Polysaccharide resin) were added. Next iron oxide and polymethyl methacrylate isopropyl titanium triisostearate were added, one at a time and put in the Homomixer until dispersed, about 30–45 minutes at a temperature of about 85° C. to 90° C.

(B) All the ingredients in sequence B were weighed and heated to 85 to 90° C. The resulting composition was emulsified with a paddle mixer, adding the product of sequence B to the product of sequence A above, for 15 minutes. The resulting combination was cooled to 60° C.

(C) All the ingredients in sequence (C) were added to the combination of A and B at 600° C.

(D) All the ingredients in sequence (D) were added to the A-B-C combination at 55° C.

(E) All the ingredients in sequence (E) were added to the A-B-C-D combination at 45° C.

(F) All the ingredients in sequence (F) were added to the A-B-C-D-E combination at 45° C.

The A-B-C-D-E-F combination composition was cooled to 30–35° C. The mascara composition formed had a creamy texture, glossy appearance, and when applied to eyelashes, provided a deep, rich color, enhanced the eyelashes so they appeared thicker and longer, and applied comfortably, with no clumping or stickiness.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. A composition comprising:
   at least one organic phospholipid capable of forming bilayers in aqueous solution;
   at least one amphoteric surfactant; and
   at least one nonionic surfactant present in an amount by weight equal to or greater than the amount of said at least one phospholipid.

2. A composition according to claim 1, wherein said composition further comprises water.

3. A composition according to claim 1, wherein said at least one nonionic surfactant is present in an amount by weight greater than the amount of said at least one phospholipid.

4. A composition according to claim 1, wherein said at least one amphoteric surfactant is present in an amount by weight greater than the amount of said at least one phospholipid.

5. A composition according to claim 1, wherein said at least one organic phospholipid capable of forming bilayers in aqueous solution is a lecithin.

6. A composition according to claim 1, wherein said at least one phospholipid, said at least one amphoteric surfactant, and said at least one nonionic surfactant are present in a combined amount sufficient to allow at least one water-insoluble ingredient to be incorporated into an aqueous solution.

7. A composition according to claim 6, wherein said at least one water-insoluble ingredient is selected from unneutralized and partially neutralized water-insoluble polymers, resins, and latexes.

8. A composition according to claim 7, wherein said water-insoluble polymers, resins, and latexes contain at least one carboxyl moiety.

9. A composition according to claim 6, wherein said at least one water-insoluble ingredient is a lipophilic ingredient.

10. A composition according to claim 6, wherein said lipophilic ingredient is a silicone, oil-soluble vitamin, ceramide, natural oil, a sunscreen, or a mixture thereof.

11. A composition according to claim 1, wherein said at least one nonionic surfactant is formed from at least a $C_8$ to $C_{24}$ fatty alcohol, a $C_8$ to $C_{24}$ fatty acid, or a $C_8$ to $C_{24}$ glyceride.

12. A composition according to claim 1, wherein said at least one nonionic surfactant has an HLB of at least 10.

13. A composition according to claim 1, wherein said at least one amphoteric surfactant is selected from betaines, sultaines, hydroxysultaines, alkyl amphodiacetates, alkyl amphodipropionates, imidazolines, and salts thereof.

14. A composition according to claim 13, wherein said at least one amphoteric surfactant is cocoamphodipropionate or cocamidopropyl hydroxysultaine.

15. A composition according to claim 1, wherein said at least one organic phospholipid is present in an amount of greater than 0 to 5% by weight relative to the total weight of the composition.

16. A composition according to claim 12, wherein said at least one organic phospholipid is present in an amount of 5% by weight relative to the total weight of the composition.

17. A composition according to claim 1, wherein said at least one nonionic surfactant is present in an amount of 5% to 20% by weight relative to the total weight of the composition.

18. A composition according to claim 17, wherein said at least one nonionic surfactant is present in an amount of 10% to 20% by weight relative to the total weight of the composition.

19. A composition according to claim 1, wherein said at least one amphoteric surfactant is present in an amount of 2% to 25% by weight relative to the total weight of the composition.

20. A composition according to claim 7, wherein said at least one amphoteric surfactant is present in an amount of 6% to 25% by weight relative to the total weight of the composition.

21. A composition according to claim 9, wherein said at least one amphoteric surfactant is present in an amount of 4% to 20% by weight relative to the total weight of the composition.

22. A composition according to claim 1, wherein said at least one organic phospholipid, said at least one amphoteric surfactant, and said at least one nonionic surfactant are present in a ratio of 1:0.8:2 and above by weight.

23. A composition according to claim 7, wherein said at least one organic phospholipid, said at least one amphoteric surfactant, and said at least one nonionic surfactant are present in a ratio of 1:1.2:3 and above by weight.

24. A composition according to claim 23, wherein said at least one organic phospholipid, said at least one amphoteric surfactant, and said at least one nonionic surfactant are present in a ratio of 1:1.2:4 and above by weight.

25. A composition according to claim 9, wherein said at least one organic phospholipid, said at least one amphoteric surfactant, and said at least one nonionic surfactant are present in a ratio of from 1:1.2:2 and above by weight.

26. A delivery system for water-insoluble ingredients comprising:
   at least one organic phospholipid capable of forming bilayers in aqueous solution;
   at least one amphoteric surfactant;
   at least one nonionic surfactant;
   at least one water-insoluble ingredient; and
   an aqueous phase,
wherein said at least one organic phospholipid, said at least one amphoteric surfactant, and said at least one nonionic surfactant are present in a combined amount sufficient to allow said at least one water-insoluble ingredient to be incorporated into said system.

27. A delivery system for water-insoluble ingredients according to claim 26, wherein said at least one nonionic surfactant is present in an amount by weight equal to or greater than the amount of said at least one organic phospholipid.

28. A delivery system according to claim 26, wherein said aqueous phase further comprises additional ingredients selected from anionic surfactants, organic salts, inorganic salts, proteins, hair dyes, water-soluble polymers, and amino acids.

29. A delivery system according to claim 26, wherein said at least one water-insoluble ingredient is selected from unneutralized and partially neutralized water-insoluble polymers, resins, and latexes.

30. A delivery system according to claim 29, wherein said water-insoluble polymers, resins, and latexes contain at least one carboxyl moiety.

31. A delivery system according to claim 26, wherein said at least one water-insoluble ingredient is a lipophilic ingredient.

32. A delivery system according to claim 31, wherein said lipophilic ingredient is a silicone, oil-soluble vitamin, ceramide, natural oil, a sunscreen or a mixture thereof.

33. A delivery system according to claim 26, wherein said at least one organic phospholipid capable of forming bilayers in aqueous solution is a lecithin.

34. A delivery system according to claimed 26, wherein said at least one nonionic surfactant is formed from a $C_8$ to $C_{24}$ fatty alcohol, a $C_8$ to $C_{24}$ fatty acid, or a $C_8$ to $C_{24}$ glyceride.

35. A delivery system according to claim 26, wherein said at least one nonionic surfactant has an HLB of at least 10.

36. A delivery system according to claim 26, wherein said at least one amphoteric surfactant is selected from betaines, sultaines, hydroxysultaines, alkyl amphodiacetates, alkyl amphodipropionates, imidazolines, and salts thereof.

37. A delivery system according to claim 36, wherein said at least one amphoteric surfactant is cocoamphodipropionate or cocamidopropyl hydroxysultaine.

38. A delivery system according to claim 26, wherein said at least one organic phospholipid is present in an amount of greater than 0 to 5% by weight relative to the total weight of said delivery system.

39. A delivery system according to claim 38, wherein said at least one organic phospholipid is present in an amount of 5% by weight relative to the total weight of said delivery system.

40. A delivery system according to claim 27, wherein said at least one nonionic surfactant is present in an amount of 5% to 20% by weight relative to the total weight of said delivery system.

41. A delivery system according to claim 40, wherein said at least one nonionic surfactant is present in an amount of 10% to 20% by weight relative to the total weight of said delivery system.

42. A delivery system according to claim 27, wherein said at least one amphoteric surfactant is present in an amount of 2% to 25% by weight rlative to the total weight of said delivery system.

43. A delivery system according to claim 29, wherein said at least one amphoteric surfactant is present in an amount of 6% to 25% by weight relative to the total weight of said delivery system.

44. A delivery system according to claim 31, wherein said at least one amphoteric surfactant is present in an amount of 4% to 20% by weight relative to the total weight of said delivery system.

45. A delivery system according to claim 27, wherein said at least one organic phospholipid, said at least one amphoteric surfactant, and said at least one nonionic surfactant are present in a ratio of 1:0.8:2 and above by weight.

46. A delivery system according to claim 29, wherein said at least one organic phospholipid, said at least one amphoteric surfactant, and said at least one nonionic surfactant are present in a ratio of 1:1.2:3 and above by weight.

47. A delivery system according to claim 46, wherein said at least one organic phospholipid, said at least one amphoteric surfactant, and said at least one nonionic surfactant are present in a ratio of 1:1.2:4 and above by weight.

48. A delivery system according to claim 31, wherein said at least one organic phospholipid, said at least one amphoteric surfactant, and said at least one nonionic surfactant are present in a ratio of from 1:1.2:2 and above by weight.

49. A delivery system according to claim 26, wherein said at least one organic phospholipid is a lecithin, said at least one nonionic surfactant is selected from PPG-5-Ceteth-20 and Oleth-10, said at least one amphoteric surfactant is disodium cocoamphodipropionate.

50. A delivery system according to claim 26, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

51. A delivery system according to claim 50, wherein said make-up composition is a mascara or a foundation.

52. A process for the preparation of a delivery system as claimed in claim 26, said process comprising the following steps:
  (a) combining said organic phospholipid, said nonionic surfactant, and said amphoteric surfactant to obtain a mixture;
  (b) heating the mixture obtained in step (a);
  (c) adding an aqueous solution to form a diluted mixture; and
  (d) cooling said diluted mixture.

53. The process of claim 52, wherein a water-insoluble ingredient is added to the mixture of step (a).

54. A method for treating keratinous substances, said method comprising:
  preparing an aqueous solution comprising at least one organic phospholipid capable of forming bilayers in aqueous solution; at least one amphoteric surfactant; at least one nonionic surfactant present in an amount by weight equal to or greater than the amount of said at least one phospholipid; and at least one water-insoluble ingredient, wherein said at least one organic phospholipid, said at least one amphoteric surfactant, and said at least one nonionic surfactant are present in a combined amount sufficient to allow said water-insoluble ingredient to be incorporated into said aqueous solution; and
  applying said aqueous solution to said keratinous substances.

55. A method according to claim 54, wherein said treating comprises shampooing, conditioning, dyeing, bleaching, permanent waving, relaxing, setting, moisturizing, and making-up.

56. A method according to claim 55, wherein said keratinous substances comprise hair, skin, and eyelashes.

57. A method according to claim 55, wherein making-up comprises applying mascara to the eyelashes or foundation to facial skin.

58. A composition comprising:
  at least one organic phospholipid capable of forming bilayers in aqueous solution;
  at least one amphoteric surfactant;
  at least one nonionic surfactant present in an amount by weight equal to or greater than the amount of said at least one phospholipid;
  at least one polysaccharide resin; and
  at least one pigment.

59. A composition comprising:
  at least one organic phospholipid capable of forming bilayers in aqueous solution;
  at least one amphoteric surfactant;
  at least one nonionic surfactant present in an amount by weight equal to or greater than the amount of said at least one phospholipid;
  at least one polysaccharide resin; and
  at least one film former other than said at least one polysaccharide resin.

60. A composition according to claim 59, wherein said composition further comprises a pigment.

* * * * *

UNITED STATES PATENT AND TRADEMARK OFFICE
CERTIFICATE OF CORRECTION

PATENT NO. : 6,221,389 B1
DATED : April 24, 2001
INVENTOR(S) : David W. Cannell et al.

It is certified that error appears in the above-identified patent and that said Letters Patent is hereby corrected as shown below:

Column 30, claim 34,
Line 19, "claimed 26" should read -- claim 26 --.

Column 30, claim 42,
Line 50, "rlative" should read -- relative --.

Column 32, claim 56,
Line 13, "claim 55" should read -- claim 54 --.

Signed and Sealed this

Eleventh Day of December, 2001

Attest:

*Nicholas P. Godici*

NICHOLAS P. GODICI
*Attesting Officer*  *Acting Director of the United States Patent and Trademark Office*